US008007677B2

(12) United States Patent
Knapp et al.

(10) Patent No.: US 8,007,677 B2
(45) Date of Patent: Aug. 30, 2011

(54) AZEOTROPE COMPOSITIONS COMPRISING 1,1,1,2,3-PENTAFLUOROPROPENE AND HYDROGEN FLUORIDE AND USES THEREOF

(75) Inventors: Jeffrey P. Knapp, Wilmington, DE (US); Barry Asher Mahler, Glen Mills, PA (US); Velliyur Nott Mallikarjuna Rao, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 54 days.

(21) Appl. No.: 12/440,068

(22) PCT Filed: Sep. 7, 2007

(86) PCT No.: PCT/US2007/019657
§ 371 (c)(1), (2), (4) Date: Mar. 5, 2009

(87) PCT Pub. No.: WO2008/030615
PCT Pub. Date: Mar. 13, 2008

(65) Prior Publication Data
US 2010/0187464 A1 Jul. 29, 2010

Related U.S. Application Data

(60) Provisional application No. 60/843,020, filed on Sep. 8, 2006.

(51) Int. Cl.
| A62D 1/00 | (2006.01) |
| C09K 5/00 | (2006.01) |
| C09K 5/04 | (2006.01) |
| B01F 1/00 | (2006.01) |
| C23G 5/00 | (2006.01) |
| H01B 3/24 | (2006.01) |
| B01D 3/34 | (2006.01) |
| C07C 17/00 | (2006.01) |
| C07C 17/25 | (2006.01) |
| C07C 19/08 | (2006.01) |
| C07C 21/18 | (2006.01) |
| C07C 17/38 | (2006.01) |
| C11D 17/00 | (2006.01) |
| C11D 17/08 | (2006.01) |

(52) U.S. Cl. .............. 252/2; 252/67; 252/364; 252/570; 203/29; 203/38; 570/155; 570/178; 510/408; 510/415

(58) Field of Classification Search ......... 252/2, 182.11, 252/67, 364, 570; 510/408, 415; 570/155, 570/178; 203/29, 38
See application file for complete search history.

(56) References Cited

U.S. PATENT DOCUMENTS

| 5,396,000 A | 3/1995 | Nappa et al. |
| 5,679,875 A | 10/1997 | Aoyama |
| 6,031,141 A | 2/2000 | Mallikarjuna et al. |
| 6,369,284 B1 * | 4/2002 | Nappa et al. ............... 570/156 |
| 6,858,571 B2 * | 2/2005 | Pham et al. ............... 510/408 |
| 2006/0106263 A1 | 5/2006 | Miller et al. |

FOREIGN PATENT DOCUMENTS

| WO | 9926908 A1 | 6/1999 |
| WO | 2006050215 A2 | 5/2006 |
| WO | WO 2006050215 A2 * | 5/2006 |
| WO | 2007053688 A2 | 5/2007 |

OTHER PUBLICATIONS

Harold R. Null, Phase Equilibrium in Process Design, 1970, pp. 124-126, Wiley-Interscience.
Reid et al., The Properties of Gases and Liquids, pp. 241-387, Fourth Edition, McGraw-Hill, 1987.
Stanley M. Walas, Phase Equilibria in Chemical Engineering, 1985, pp. 165-244, Butterworth Publishers.
U.S. Appl. No. 11/264,183, filed Nov. 1, 2005, Applicant: Ralph Newton Miller et al.
U.S. Appl. No. 60/830,939, filed Jul. 31, 2006, Mario Joseph Nappa et al.

* cited by examiner

*Primary Examiner* — Lorna M Douyon
*Assistant Examiner* — Tanisha Diggs (57) ABSTRACT

Disclosed herein are azeotrope and near-azeotrope compositions comprising E-1,1,1,2,3-pentafluoropropene (E-HFC-1225ye) and hydrogen fluoride. The azeotrope and near-azeotrope compositions are useful in processes to produce and in processes to purify E-HFC-1225ye and/or Z-1,1,1,2,3-pentafluoropropene (Z-HFC-1225ye). Also disclosed are processes for the extractive distillation to separate E-HFC-1225ye from Z-HFC-1225ye.

11 Claims, 4 Drawing Sheets

AZEOTROPE COMPOSITIONS COMPRISING 1,1,1,2,3-PENTAFLUOROPROPENE AND HYDROGEN FLUORIDE AND USES THEREOF

This is an application filed under 35 U.S.C. 371 of PCT/US07/19657, filed Sep. 7, 2007, which claim benefit of U.S. Application No. 60/843,020, filed Sep. 8, 2006.

BACKGROUND OF THE INVENTION

1. Field of the Invention

Disclosed herein are azeotrope compositions comprising E-1,1,1,2,3-pentafluoropropene and hydrogen fluoride. The azeotrope compositions are useful in processes to produce E-1,1,1,2,3-pentafluoropropene and in processes to purify E-1,1,1,2,3-pentafluoropropene.

2. Description of Related Art

Chlorine-containing compounds, such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, or fluoroolefins, containing one or more hydrogens in the molecule, are being considered for use in some of the applications, like for example, in refrigeration. Thus, there is a need for additional commercially acceptable methods of manufacturing and purifying fluoroolefins.

BRIEF SUMMARY OF THE INVENTION

In one embodiment of the present invention an azeotrope or near-azeotrope composition is provided comprising E-HFC-1225ye and hydrogen fluoride.

In another embodiment, a process is provided for the separation of E-HFC-1225ye from HFC-236 comprising (a) forming a mixture of E-HFC-1225ye, HFC-236, and hydrogen fluoride; and (b) subjecting said mixture to a distillation step forming a column distillate composition comprising an azeotrope or near-azeotrope composition of hydrogen fluoride and E-HFC-1225ye essentially free of HFC-236.

In another embodiment, a process is provided for the separation of E-HFC-1225ye from a mixture comprising an azeotrope composition of E-HFC-1225ye and hydrogen fluoride, said process comprising (a) subjecting said mixture to a first distillation step in which a composition enriched in either (i) hydrogen fluoride or (ii) E-HFC-1225ye is removed as a first distillate composition with a first bottoms composition being enriched in the other of said components (i) or (ii); and (b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

In another embodiment, a process is provided for separating E-HFC-1225ye from a mixture comprising hydrogen fluoride and E-HFC-1225ye, said process comprising (a) contacting a first composition comprising E-HFC-1225ye and hydrogen fluoride with an entraining agent to form a second composition; (b) distilling the second composition thereby separating E-HFC-1225ye from hydrogen fluoride and entraining agent; and (c) recovering E-HFC-1225ye product essentially free of hydrogen fluoride.

In another embodiment, a process is provided for the purification of E-HFC-1225ye from a mixture of E-HFC-1225ye, HFC-236, and hydrogen fluoride, said process comprising (a) subjecting said mixture to a first distillation step to form a first distillate comprising an azeotrope or near-azeotrope composition containing E-HFC-1225ye and hydrogen fluoride and a first bottoms comprising HFC-236; (b) subjecting said first distillate to a second distillation step from which a composition enriched in either (i) hydrogen fluoride or (ii) E-HFC-1225ye is removed as a second distillate composition with a second bottoms composition being enriched in the other of said components (i) or (ii); and (c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

In another embodiment, a process is provided to produce E-HFC-1225ye essentially free of HF and HFC-236 comprising (a) feeding HFC-236 to a reaction zone for dehydrofluorination to form a reaction product composition comprising E-HFC-1225ye, unreacted HFC-236 and hydrogen fluoride; (b) subjecting said reaction product composition to a first distillation step to form a first distillate composition comprising an azeotrope or near-azeotrope composition containing E-HFC-1225ye and hydrogen fluoride and a first bottoms composition comprising HFC-236; (c) subjecting said first distillate composition to a second distillation step from which a composition enriched in either (i) hydrogen fluoride or (ii) E-HFC-1225ye is removed as a second distillate composition with a second bottoms composition being enriched in the other of said components (i) or (ii); and (d) subjecting said second distillate composition to a third distillation step conducted at a different pressure than the second distillation step in which the component enriched in the second bottoms composition in (c) is removed in a third distillate composition with a third bottoms composition enriched in the same component that was enriched in the second distillate composition.

In another embodiment, a process is provided for separating E-1,1,1,2,3-pentafluoropropene (E-HFC-1225ye) from a first mixture comprising E-1,1,1,2,3-pentafluoropropene (E-HFC-1225ye) and Z-1,1,1,2,3-pentafluoropropene (Z-HFC-1225ye), comprising the steps of (a) contacting said first mixture with at least one extractive agent, to form a second mixture, (b) distilling said second mixture, and (c) recovering E-1,1,1,2,3-pentafluoropropene (E-HFC-1225ye) essentially free of Z-1,1,1,2,3-pentafluoropropene (Z-HFC-1225zc).

The foregoing general description and the following detailed description are exemplary and explanatory only and are not restrictive of the invention, as defined in the appended claims.

DETAILED DESCRIPTION OF THE INVENTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the descriptions of azeotrope and near-azeotrope compositions, azeotropic distillation for separation of E-HFC-1225ye and HFC-236, pressure swing distillation for separation of E-HFC1225ye from a mixture of E-HFC-1225ye and HF, process for separation of E-HFC-1225ye from mixtures of E-HFC-1225ye, HFC-236 and HF, process to produce E-HFC-1225ye essentially free of HF and HFC-236, azeotropic distillation with no added entraining agent for separation of E-HFC-1225ye and HF, azeotropic distillation with an entraining agent for separation of E-HFC-1225ye and HF, extractive distillation to separate E-HFC-1225ye and Z-HFC-1225ye, and finally Examples.

DEFINITIONS AND CLARIFICATION OF TERMS

Before addressing details of embodiments described below, some terms are defined or clarified.

Anhydrous hydrogen fluoride (HF) has CAS reg. no. 7664-39-3 and is commercially available.

Disclosed herein are compositions containing 1,1,1,2,3-pentafluoropropene (HFC-1225ye, $CF_3CF=CHF$) and processes related to HFC-1225ye. HFC-1225ye may exist as one of two configurational isomers, E or Z. HFC-1225ye as used herein may refer to either E-HFC-1225ye or Z-HFC-1225ye or any mixture or combination thereof. E-HFC-1225ye as used herein refers to a mixture of the isomers, E-HFC-1225ye (CAS reg no. 5595-10-8) and Z-HFC-1225ye (CAS reg. no. 5528-43-8) wherein the predominant isomer is E-HFC-1225ye. E-HFC-1225ye may be prepared by methods known in the art, such as those described in U.S. Pat. Nos. 5,396,000, 5,679,875, 6,031,141, and 6,369,284, all of which are incorporated herein by reference.

As used herein, predominant isomer is intended to mean that isomer which is present in the composition at a concentration of greater than 50 mole percent, greater than 60 mole percent, greater than 70 mole percent, greater than 80 mole percent, or greater than 90 mole percent.

Disclosed herein are processes related to 1,1,1,2,3,3-hexafluoropropane (HFC-236ea, CAS reg. no. 431-63-0) and 1,1,1,2,2,3-hexafluoropropane (HFC-236cb, CAS reg. no. 677-56-5). HFC-236ea and HFC-236cb may be prepared by methods known in the art. As used herein HFC-236 refers to either HFC-236ea or HFC-236cb or any mixture or combination thereof.

By azeotropic or azeotrope composition is meant a constant-boiling mixture of two or more substances that boils at a constant composition and thus behaves as a single substance. Constant-boiling compositions are characterized as azeotropic because they exhibit either a maximum or minimum boiling point, when compared with the boiling points of the individual components. Azeotropic compositions are also characterized by a minimum or a maximum in the vapor pressure measurements relative to the vapor pressure of the neat components in a PTx cell as a function of composition at a constant temperature. For homogenous azeotropes, where the vapor phase is in equilibrium with a single liquid phase, the compositions of the vapor and liquid phases are identical. However, for heterogeneous azeotropes, where the vapor phase is in equilibrium with two liquid phases, all three equilibrium phases can have different, but constant, compositions.

As used herein, the term "azeotrope-like composition" (also commonly referred to as a "near azeotropic composition") means a constant boiling, or substantially constant boiling liquid admixture of two or more substances that behaves as a single substance. One way to characterize an azeotrope-like composition is that the composition of the vapor produced by partial evaporation or distillation of the liquid does not change substantially throughout the partial evaporation or distillation. Similarly, the composition of the liquid phase or phases present does not change substantially during the partial evaporation or distillation. That is, the admixture boils/distills/refluxes without substantial composition change. This is to be contrasted with non-azeotrope-like compositions in which the liquid composition changes to a substantial degree during boiling or evaporation. Another way to characterize an azeotrope-like composition is that the bubble point vapor pressure of the composition and the dew point vapor pressure of the composition at a particular temperature are substantially the same. Herein, a composition is considered to be azeotrope-like if the difference in dew point pressure and bubble point pressure is less than or equal to 3 percent (based upon the bubble point pressure).

By high-boiling azeotrope is meant that an azeotropic or azeotrope-like composition boils at a higher temperature at any given pressure than any one of the compounds that comprise it would separately boil at that pressure. Alternately, by high-boiling azeotrope is meant any azeotropic or azeotrope-like composition that has a lower vapor pressure at any given temperature than any one of the compounds that comprise it would separately have at that temperature.

By low-boiling-azeotrope is meant that an azeotropic or azeotrope-like composition boils at a lower temperature at any given pressure than any one of the compounds that comprise it would separately boil at that pressure. Alternately, by low-boiling azeotrope is meant any azeotropic or azeotrope-like composition that has a higher vapor pressure at any given temperature than the vapor pressure of any one of the compounds that comprise the azeotrope would separately have at that temperature.

It is possible to characterize an azeotropic or azeotrope-like composition as a substantially constant-boiling admixture that may appear under many guises, depending upon the conditions chosen, by several criteria:

The composition can be defined as an azeotrope of two compounds because the term "azeotrope" is at once both definitive and limitative, and requires effective amounts of those two or more compounds for this unique composition of matter which can be a constant-boiling composition.

It is well known by those skilled in the art, that at different pressures, the composition of a given azeotrope or azeotrope-like composition will vary at least to some degree, as will the boiling point temperature. Thus, an azeotropic or azeotrope-like composition of two compounds represents a unique type of relationship but with a variable composition which depends on temperature and/or pressure. Therefore, compositional ranges, rather than fixed compositions, are often used to define azeotropes and azeotrope-like compositions.

An azeotrope or azeotrope-like composition of two compounds can be characterized by defining compositions characterized by a boiling point at a given pressure, thus giving identifying characteristics without unduly limiting the scope of the invention by a specific numerical composition, which is limited by and is only accurate as the analytical equipment available.

It is recognized in the art that both the boiling point and the weight (or mole) percentages of each component of the azeotropic composition may change when the azeotrope or azeotrope-like liquid composition is allowed to boil at different pressures. Thus, an azeotropic or an azeotrope-like composition may be defined in terms of the unique relationship that exists among components or in terms of the exact weight (or mole) percentages of each component of the composition characterized by a fixed boiling point at a specific pressure.

As used herein, the term "azeotrope" is meant to refer to azeotrope compositions and/or azeotrope-like compositions.

As used herein, by "essentially free of" is meant that a composition contains less than about 100 ppm (mole basis), less than about 10 ppm or less than about 1 ppm, of the specified component. If a composition is essentially free of more than one component, then the total concentration of those components is less than about 100 ppm, less than about 10 ppm, or less than about 1 ppm.

By essentially pure, it is meant that a composition contains less than about 100 parts per million by weight (ppm) of any impurities, and preferably less than about 10 ppm of any impurities, and more preferably less than about 1 ppm of any impurities. By impurity (or impurities) is meant any fluorinated compound(s) other than the main component of the composition that may be present in the composition.

By conventional distillation is meant that only the relative volatilities of the components of the mixture to be separated are used to separate the components.

By azeotropic distillation is meant a process in which a distillation column is operated under conditions to cause one or more azeotropic or azeotrope-like composition to form, and thereby facilitates the separation of the components of the mixture. Azeotropic distillations may occur where only the components of the mixture to be separated are distilled, or where an entraining agent is added that forms an azeotrope with one or more of the components of the initial mixture. Entraining agents that act in this manner, that is to say, that form an azeotrope with one of more of the components of the mixture to be separated thus facilitating the separation of those components by distillation, are more commonly called azeotroping agents or azeotropic entraining agents.

The term "entraining agent" is used herein to describe any compound that would be effective in separation of E-HFC-1225ye from mixtures comprising HF and E-HFC-1225ye in an azeotropic distillation process. Included as useful entraining agents are those compounds that form azeotropes with HF for which the boiling point is lower than the boiling point of the E-HFC-1225ye/HF azeotrope.

Entraining agents may be selected from the group consisting of hydrocarbons, chlorofluorocarbons, hydrochlorofluorocarbons, hydrofluorocarbons, perfluorocarbons, fluoroethers, HFPO, chlorine, hexafluoroacetone, methyl chloride ($CH_3Cl$), PMVE (perfluoromethylvinylether), PEVE (perfluoroethylvinylether), and mixtures thereof.

Hydrocarbon entraining agents comprise compounds containing 2 to 4 carbon atoms and hydrogen. Hydrocarbon entraining agents may be linear, branched, cyclic, saturated or unsaturated compounds. Representative hydrocarbon entraining agents include but are not limited to ethane, ethylene, acetylene, n-propane, propylene, propyne, cyclopropane, cyclopropene, propadiene, isobutane, and mixtures thereof.

Chlorofluorocarbon (CFC) entraining agents comprise compounds with carbon, chlorine and fluorine. Representative CFCs include but are not limited to dichlorodifluoromethane (CFC-12), 2-chloro-1,1,2-trifluoroethylene, chloropentafluoroethane (CFC-115), 1,2-dichloro-1,1,2,2-tetrafluoroethane, and mixtures thereof.

Hydrochlorofluorocarbon (HCFC) entraining agents comprise compounds with carbon, chlorine, fluorine and hydrogen. Representative HCFCs include but are not limited to 2-chloro-1,1-difluoroethylene (HCFC-1122), and mixtures thereof.

Hydrofluorocarbon (HFC) entraining agents comprise compounds that contain carbon, hydrogen and fluorine. Representative HFCs include but are not limited to pentafluoroethane (HFC-125), 1,1,1,2-tetrafluoroethane (HFC-134a), 1,1,1-trifluoroethane (HFC-143a), 1,1-difluoroethane (HFC-152a), fluoroethane (HFC-161), 1,1,1-trifluoropropane (HFC-236fa), 1,1,2-trifluoroethylene (HFC-1123), 1,1-difluoroethylene (HFC-1132a), 1,1,3,3,3-pentafluoropropene (HFC-1225zc), 2,3,3,3-tetrafluoropropene (HFC-1234yf), 3,3,3-trifluoropropene (HFC-1243zf), 1,3,3,3-tetrafluoropropene (HFC-1234ze, either of the two isomers, E- or Z- or mixtures thereof), and mixtures thereof.

Perfluorocarbon (PFC) entraining agents comprise compounds with carbon and fluorine only. Representative PFCs include but are not limited to hexafluoroethane (PFC-116), octafluoropropane (PFC-218), 1,1,1,4,4,4-hexafluoro-2-propyne (PFBY-2), hexafluoropropylene (HFP, PFC-1216), hexafluorocyclopropane (PFC-C216), and mixtures thereof.

Fluoroether entraining agents comprise compounds with carbon, fluorine, optionally hydrogen and at least one ether group oxygen. Representative fluoroethers include but are not limited to trifluoromethyl-difluoromethyl ether ($CF_3OCHF_2$, HFOC-125E) fluoromethyl-trifluoromethyl ether (HFOC-134aE), difluoromethyl methyl ether ($CHF_2OCH_3$, HFOC-152aE), and mixtures thereof.

Miscellaneous other compounds that may be useful as entraining agents include HFPO, chlorine, hexafluoroacetone, methyl chloride ($CH_3Cl$), PMVE (perfluoromethylvinylether), PEVE (perfluoroethylvinylether).

Entraining agents as described above are available commercially or may be produced by methods known in the art.

By extractive distillation is meant a process in which an extractive agent is introduced at an upper feed point of a distillation column, whereas the mixture requiring separation is introduced at the same point or preferably, at a relatively lower feed point of the column. The substantially liquid extractive agent passes downwardly through trays or packing in the column and exits the column bottoms with one or more components of the mixture to be separated. While in the presence of the extractive agent, at least one of the components of an initial mixture to be separated becomes relatively more volatile compared to the other components of the mixture, with that more volatile component of the initial mixture exiting the column overhead. Extractive distillation may be employed when the components of a mixture have close relative volatilities that do not afford effective separation of the components by conventional distillation. In extractive distillation, at least one extractive agent is used which causes the relative volatilities of the components in a mixture to be altered such that the resultant relative volatilities, i.e., that of components of the mixture in the presence of the extractive agent, become sufficiently different to permit separation of the components by distillation techniques.

In one embodiment, extractive agents have a boiling point higher than the components being separated. In another embodiment, extractive agents suitable for separating E-HFC-1225ye from Z-HFC-1225ye have a boiling point higher than E-HFC-1225ye and Z-HFC-1225ye. In another embodiment, extractive agents suitable for use separating E-HFC-1225ye from Z-HFC-1225ye have a boiling point about 20° C. to about 50° C. higher than E-HFC-1225ye and Z-HFC-1225ye. In another embodiment, the extractive agents suitable for use separating E-HFC-1225ye from Z-HFC-1225ye are selected from the group consisting of hydrocarbons, cyclic hydrocarbon ethers, non-cyclic hydrocarbon ethers, alcohols, ketones, and esters.

Hydrocarbon extractive agents of the present invention comprise compounds having only carbon and hydrogen, with about 4 to about 10 carbon atoms. Hydrocarbon extractive agents may be linear, branched, or cyclic and may be saturated or unsaturated compounds. Representative hydrocarbon extractive agents include but are not limited to n-pentane, 2-methylbutane, cyclopentane, 1-pentene, 2-pentene, n-hexane, 2-methylpentane, 3-methylpentane, 2,2-dimethylbutane, 2,3-dimethylbutane, 2,2-dimethylhexane, 2,4-dimethylhexane, 2,5-dimethylhexane, 3,4-dimethylhexane, and cyclohexane.

Cyclic hydrocarbon ethers used as extractive agents with the present invention have from 2 to 6 carbon atoms. Cyclic hydrocarbon ethers in this invention denote cyclic ethers consisting of C, H and O, wherein the number of carbon atoms is from 2 to 6. Examples of these compounds include furan, tetrahydrofuran (THF), ethylene oxide, propylene oxide (1,2-epoxypropane), oxetane and tetrahydropyran.

Non-cyclic hydrocarbon ethers used as extractive agents with the present invention have the formula $C_xH_{2x+1}OC_yH_{2y+1}$ wherein x and y are 1 or greater and x+y is from 3 to 6. Examples of these compounds include diethyl ether, diisopropyl ether and methyl tert-butyl ether.

Alcohols used as extractive agents with the present invention have the formula $C_zH_{2z+1}OH$ wherein z is from 1 to 4. Examples of these compounds include methanol, ethanol, n-propanol, and iso-propanol.

Ketones used as extractive agents with the present invention have the formula $C_mH_{2m+1}C(O)C_nH_2n+1$ wherein m and n are 1 or greater and m+n is at most 5. Examples of these compounds include acetone and butanone.

Ester extractive agents comprise compounds formed by reaction of an acid and an alcohol. Carboxylate esters are those formed by reaction of a carboxylic acid. Ester extractive agents include carboxylate esters such as methyl formate, ethyl formate, propyl formate, isopropyl formate, methyl acetate, ethyl acetate, propyl acetate, isopropyl acetate, methyl propionate, ethyl propionate, propyl propionate, methyl butyrate, and ethyl butyrate. Ester extractive agents also include esters formed from inorganic acids, including dimethyl carbonate, dimethyl sulfate and the like.

Azeotrope and Near-Azeotrope Compositions

In considering a process for the dehydrofluorination of HFC-236 to E-HFC-1225ye and HF and the isolation of E-HFC-1225ye from such a process, it has been discovered surprisingly that the hydrofluoroolefin E-HFC-1225ye forms an azeotrope with HF.

In one embodiment, a composition is provided, which comprises E-HFC-1225ye and an effective amount of hydrogen fluoride (HF) to form an azeotrope composition. By effective amount is meant an amount, which, when combined with E-HFC-1225ye, results in the formation of an azeotrope or near-azeotrope mixture. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

Compositions may be formed that comprise azeotrope combinations of hydrogen fluoride with E-HFC-1225ye. These include compositions comprising from about 37.4 mole percent to about 39.8 mole percent HF and from about 62.6 mole percent to about 60.2 mole percent E-HFC-1225ye (which forms an azeotrope boiling at a temperature from between about −50° C. and about 120° C. and at a pressure from between about 2.7 psi (18.7 kPa) to about 613 psi (4226 kPa)).

Additionally, near-azeotrope compositions containing HF and E-HFC-1225ye may also be formed. Such near-azeotrope compositions comprise about 49.8 mole percent to about 99.0 mole percent E-HFC-1225ye and about 50.2 mole percent to about 1.0 mole percent HF at temperatures ranging from about −40° C. to about 120° C. and at pressures from about 4.9 psi (38.2 kPa) to about 613 psi (4226 kPa).

Compositions may be formed that consist essentially of azeotrope combinations of hydrogen fluoride with E-HFC-1225ye. These include compositions consisting essentially of from about 37.4 mole percent to about 39.8 mole percent HF and from about 62.6 mole percent to about 60.2 mole percent E-HFC-1225ye (which forms an azeotrope boiling at a temperature from between about −50° C. and about 120° C. and at a pressure from between about 2.7 psi (18.7 kPa) to about 613 psi (4226 kPa)).

Near azeotrope compositions may also be formed that consist essentially of about 49.8 mole percent to about 99.0 mole percent E-HFC-1225ye and about 50.2 mole percent to about 1.0 mole percent HF at temperatures ranging from about −40° C. to about 120° C. and at pressures from about 4.9 psi (38.2 kPa) to about 613 psi (4226 kPa).

At atmospheric pressure, the boiling points of hydrofluoric acid and E-HFC-1225ye are about 19.5° C. and about −15° C., respectively. The relative volatility at 62.6 psi (432 kPa) and about 20° C. of HF and E-HFC-1225ye may be calculated to be nearly 1.0 as 37.5 mole percent HF and 62.5 mole percent E-HFC-1225ye is approached. The calculations indicate that the use of conventional distillation procedures may not result in the separation of a substantially pure compound because of the low value of relative volatility of the compounds.

To determine the relative volatility of HF with E-HFC-1225ye, the so-called PTx Method is used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, are obtained and are analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", $4^{th}$ Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and E-HFC-1225ye behave in an ideal manner, and can sufficiently predict the relative volatilities of the components in such mixtures. Thus, while HF may have a good relative volatility compared to E-HFC-1225ye at low E-HFC-1225ye concentrations, the relative volatility may become nearly 1.0 as 62.5 mole percent E-HFC-1225ye is approached at about 20° C. This would make it impossible to separate E-HFC-1225ye from HF by conventional distillation from such a mixture. Where the relative volatility approaches 1.0 defines the system as forming a near-azeotrope or azeotrope composition.

It may be calculated that azeotropes of E-HFC-1225ye and HF are formed at a variety of temperatures and pressures. An azeotrope of HF and E-HFC-1225ye is found at about 19.5° C. and 62.6 psi (432 kPa) consisting essentially of about 37.5 mole percent HF and about 62.5 mole percent E-HFC-1225ye. Based upon the above findings, azeotrope compositions at other temperatures and pressures may be calculated. It has been calculated that an azeotrope composition of about 39.8 mole percent HF and about 60.2 mole percent E-HFC-1225ye can be formed at −40° C. and 4.9 psi (38.2 kPa) and an azeotrope composition of about 38.5 mole percent HF and about 61.5 mole percent E-HFC-1225ye can be formed at 120° C. and 613 psi (4226 kPa).

It may also be calculated that azeotrope or near-azeotrope compositions may be formed between about 4.9 psi (38.2 kPa) to about 613 psi (4226 kPa) at temperatures ranging from about −40° C. to about 120° C., said compositions consisting essentially of about 49.8 mole percent to about 99.0 mole percent E-HFC-1225ye and about 50.2 mole percent to about 1.0 mole percent HF.

The HF/E-HFC-1225ye azeotrope and near-azeotrope compositions are useful in processes to produce E-HFC-1225ye and in processes to purify E-HFC-1225ye. In fact, the HF/E-HFC-1225ye azeotrope and near-azeotrope compositions may be useful in any process that creates a composition containing E-HFC-1225ye and HF.

Azeotropic Distillation for Separation of E-HFC-1225ye and HFC-236

Azeotropic distillation may be carried out to separate E-HFC-1225ye from HFC-236, which is the starting material for production of E-HFC-1225ye, by vapor phase dehydrofluorination. A pressure swing azeotropic distillation may then be carried out to separate the co-produced HF from the desired E-HFC-1225ye product. And another pressure swing azeotropic distillation may be carried out to separate HF from HFC-236. HF may be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes for removing HF from such product mixtures.

While the initial mixture treated in accordance with the processes disclosed herein can be obtained from a variety of sources, including by adding E-HFC-1225ye to HF-containing compositions, an advantageous use of the present processes resides in treating the effluent mixtures from the preparation of E-HFC-1225ye.

E-HFC-1225ye may be prepared by the vapor phase dehydrofluorination of HFC-236ea by processes known in the art, such as those described in U.S. Pat. Nos. 5,396,000, 5,679,875, 6,031,141, and 6,369,284, all of which are incorporated herein by reference. For example, HFC-1225ye can be prepared by passing HFC-236ea, HFC-236cb or mixtures thereof over a chrome oxide catalyst at elevated temperatures, for example, at above 300 deg C. The product stream from this reaction contains HFC-1225ye, HF and any unreacted HFC-236. Additionally, E-HFC-1225ye may be prepared by the vapor phase dehydrofluorination of HFC-236cb by processes such as those described in US Patent Application publication no. 2006-0106263-A1, filed Nov. 1, 2005, and in U.S. Provisional Patent Application Ser. No. 60/830,939, filed Jul. 13, 2006.

Another aspect of the present invention provides a process for the separation of E-HFC-1225ye from HFC-236 comprising: a) forming a mixture of E-HFC-1225ye, HFC-236, and hydrogen fluoride; and b) subjecting said mixture to a distillation step forming a column distillate composition comprising an azeotrope or near-azeotrope composition of HF and E-HFC-1225ye essentially free of HFC-236.

This azeotropic distillation takes advantage of the low boiling azeotrope composition formed by E-HFC-1225ye and HF. The azeotrope composition boils at a temperature lower than the boiling point of either pure component and lower than the boiling point of HFC-236 as well.

As stated previously, the mixture of E-HFC-1225ye, HFC-236 and HF may be formed by any practical means. Generally, the present process is particularly useful for the separation of E-HFC-1225ye from the reaction mixture produced by the dehydrofluorination of HFC-236. HF is a co-product formed in this dehydrofluorination reaction. The reaction mixture produced may then be treated by the instant process to remove HFC-236. The E-HFC-1225ye is taken overhead as the distillate from the distillation column as an azeotrope or near-azeotrope composition of E-HFC-1225ye with HF. The HFC-236 is taken out of the bottom of the column as a bottoms composition and may contain some amount of HF, as well. The amount of HF in the HFC-236 from the bottom of the distillation column may vary from about 35 mole percent to less than 1 part per million (ppm, mole basis) depending on the manner in which the dehydrofluorination reaction is conducted. In fact, if the dehydrofluorination reaction is conducted in a manner to provide 50 percent conversion of the HFC-236 and the reaction mixture leaving the reaction zone is fed directly to the distillation step, the HFC-236 leaving the bottom of the distillation process will contain about 34 mole percent HF.

In one embodiment, operating the present azeotropic distillation involves providing an excess of E-HFC-1225ye to the distillation column. If the proper amount of E-HFC-1225ye is fed to the column, then all the HF may be taken overhead as an azeotrope composition containing E-HFC-1225ye and HF. Thus, the HFC-236 removed from the column bottoms will be essentially free of HF.

In the distillation step, the distillate exiting the distillation column overhead comprising HF and E-HFC-1225ye may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions, which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 20 psi to about 50 psi. The distillation column is typically operated at a pressure of from about 25 psi (172 kPa) with a bottoms temperature of from about 10° C. to about 50° C. and a tops temperature of from about −20° C. to about 30° C. Normally, increasing the reflux ratio results in increased distillate stream purity, but generally the reflux ratio ranges between 1/1 and 200/1. The temperature of the condenser, which is located adjacent to the top of the column, is normally sufficient to substantially fully condense the distillate that is exiting from the top of the column, or is that temperature required to achieve the desired reflux ratio by partial condensation.

The column distillate composition comprising an azeotrope or near-azeotrope composition of HF and E-HFC-1225ye essentially free of HFC-236, must be treated to remove the HF and provide pure E-HFC-1225ye as product. This may be accomplished, for example, by neutralization or by a second distillation process, as described herein.

Pressure Swing Distillation for Separation of E-HFC1225ye from a Mixture of E-HFC-1225ye and HF A further aspect provides a process for the separation of E-HFC-1225ye from a mixture comprising an azeotrope or near-azeotrope composition of E-HFC-1225ye and HF, said process comprising: a) subjecting said mixture to a first distillation step in which a composition enriched in either (i) hydrogen fluoride or (ii) E-HFC-1225ye is removed as a first distillate composition with a first bottoms composition being enriched in the other of said components (i) or (ii); and b) subjecting said first distillate composition to a second distillation step conducted at a different pressure than the first distillation step in which the component enriched in the first bottoms composition in (a) is removed in a second distillate composition with a second bottoms composition enriched in the same component which was enriched in the first distillate composition.

The process as described above takes advantage of the change in azeotrope composition at different pressures to effectuate the separation of E-HFC-1225ye and HF. In one embodiment the first distillation step may be carried out at high pressure relative to the second distillation step. At higher pressures, the HF/E-HFC-1225ye azeotrope contains less E-HFC-1225ye. Thus, this high-pressure distillation step produces an excess of E-HFC-1225ye, which boiling at a higher temperature than the azeotrope will exit the column as the bottoms as pure E-HFC-1225ye. The first column distillate is then fed to a second distillation step operating at lower pressure. At the lower pressure, the HF/E-HFC-1225ye azeotrope shifts to lower concentrations of HF. Therefore, in this second distillation step, there exists an excess of HF. The excess HF, having a boiling point higher than the azeotrope, exits the second distillation column as the bottoms composition. The present process may be conducted in such as manner as to produce E-HFC-1225ye essentially free of HF. Additionally, the present process may be conducted in such a manner as to produce HF essentially free of E-HFC-1225ye.

Alternatively, in another embodiment, the first distillation step may be carried out at low pressure relative to the second distillation step. At lower pressures, the HF/E-HFC-1225ye azeotrope contains less HF. Thus, this low-pressure distillation step produces an excess of HF, which boiling at a higher temperature than the azeotrope will exit the column as the bottoms as pure HF. The first column distillate is then fed to a second distillation step operating at higher pressure. At the higher pressure, the HF/E-HFC-1225ye azeotrope shifts to lower concentrations of E-HFC-1225ye. Therefore, in this second distillation step, there exists an excess of E-HFC-1225ye. The excess E-HFC-1225ye, having a boiling point higher than the azeotrope, exits the second distillation column as the bottoms composition. The present process may be conducted in such as manner as to produce E-HFC-1225ye essentially free of HF. Additionally, the present process may be conducted in such a manner as to produce HF essentially free of E-HFC-1225ye.

Figure 1:
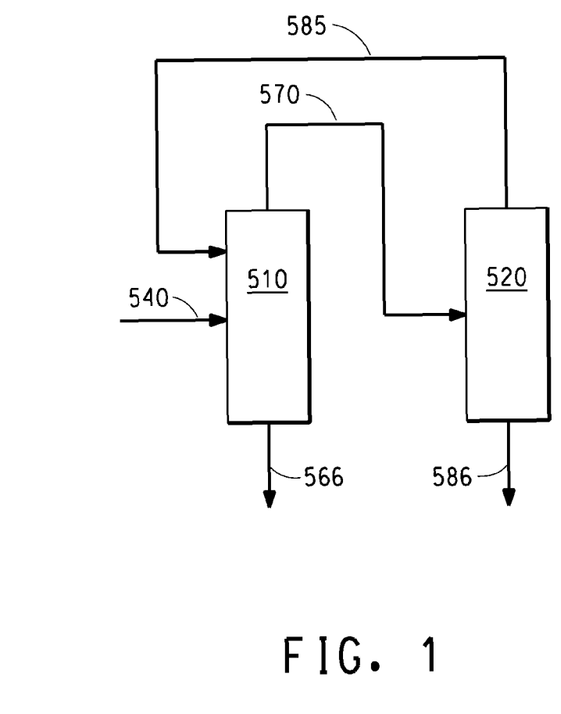
FIG. 1 illustrates one embodiment of a pressure swing azeotropic distillation (pressure swing distillation) for the separation of E-HFC-1225ye and HF.

FIG. 1 is illustrative of one embodiment for practicing the present pressure swing distillation process for the separation of E-HFC-1225ye and HF. Referring to FIG. 1, a mixture comprising HF and E-HFC-1225ye 540 is fed to the first distillation column 510. In one case, the composition of the feed lies on the E-HFC-1225ye-rich side of the azeotrope, and therefore, E-HFC-1225ye can be recovered essentially free of HF from the bottom of the first distillation column. Because the concentration of E-HFC-1225ye in the azeotrope decreases with increasing pressure, the first distillation column will operate at the higher pressure. The composition of the distillate removed from column 510 via stream 570 approaches that of the azeotrope at about 300 psi. Distillate 570 is fed to a second distillation column 520. At about 2 psi, the composition of stream 570 lies on the HF-rich side of the azeotrope so HF essentially free of E-HFC-1225ye can be removed as the bottoms product from column 520 via stream 586. The distillate from column 520 is removed via stream 585 at a composition that lies close to the azeotropic composition at about 2 psi. Distillate stream 585 is fed to the first distillation column completing the separation process.

In another embodiment, the composition of the feed lies on the HF-rich side of the azeotrope. In this embodiment, the first column would operate at the lower pressure and essentially pure HF would be removed from the process as the first column bottoms stream 566 and E-HFC-1225ye would be removed from the process as the second column bottoms.

Process for Separation of E-HFC-1225ye from Mixtures of E-HFC-1225ye, HFC-236 and HF Combination of the previously provided embodiments allows the separation of E-HFC-1225ye, HF and HFC-236 producing all three components as essentially pure E-HFC-1225ye, essentially pure HF and essentially pure HFC-236.

A further aspect provides a process for the purification of E-HFC-1225ye from a mixture of E-HFC-1225ye, HFC-236, and HF, said process comprising: a) subjecting said mixture to a first distillation step to form a first distillate comprising an azeotrope or near-azeotrope composition containing E-HFC-1225ye and HF and a first bottoms comprising HFC-236; b) subjecting said first distillate to a second distillation step from which a composition enriched in either (i) hydrogen fluoride or (ii) E-HFC-1225ye is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

Process to Produce E-HFC-1225ye Essentially Free of HF and HFC-236

A further aspect provides a process to produce E-HFC-1225ye essentially free of HF and HFC-236 comprising: a) feeding HFC-236 to a reaction zone for dehydrofluorination to form a reaction product composition comprising E-HFC-1225ye, unreacted HFC-236 and hydrogen fluoride; b) subjecting said reaction product composition to a first distillation step to form a first distillate composition comprising an azeotrope or near-azeotrope composition containing E-HFC-1225ye and HF and a first bottoms composition comprising HFC-236; c) subjecting said first distillate composition to a second distillation step from which a composition enriched in either (i) hydrogen fluoride or (ii) E-HFC-1225ye is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed in a third distillate composition with a third bottoms composition enriched in the same component that was enriched in the second distillate composition. Optionally, the process may further comprise recycling at least some portion of said first bottoms composition (HFC-236) to said reaction zone. Optionally, the process may further comprise recycling at least some portion of said second bottoms composition or third bottoms composition to said reaction zone. Optionally, the process may further comprise recycling at least some portion of said second bottoms composition or third bottoms composition to said first distillation step. Optionally, the process may further comprise recovering at least some portion of said second bottoms composition or third bottoms composition as E-HFC-1225ye essentially free of HFC-236 and HF.

The reaction zone for the dehydrofluorination may comprise a flow reactor preferably containing a fixed bed of dehydrofluorination catalyst. The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

Figure 2:
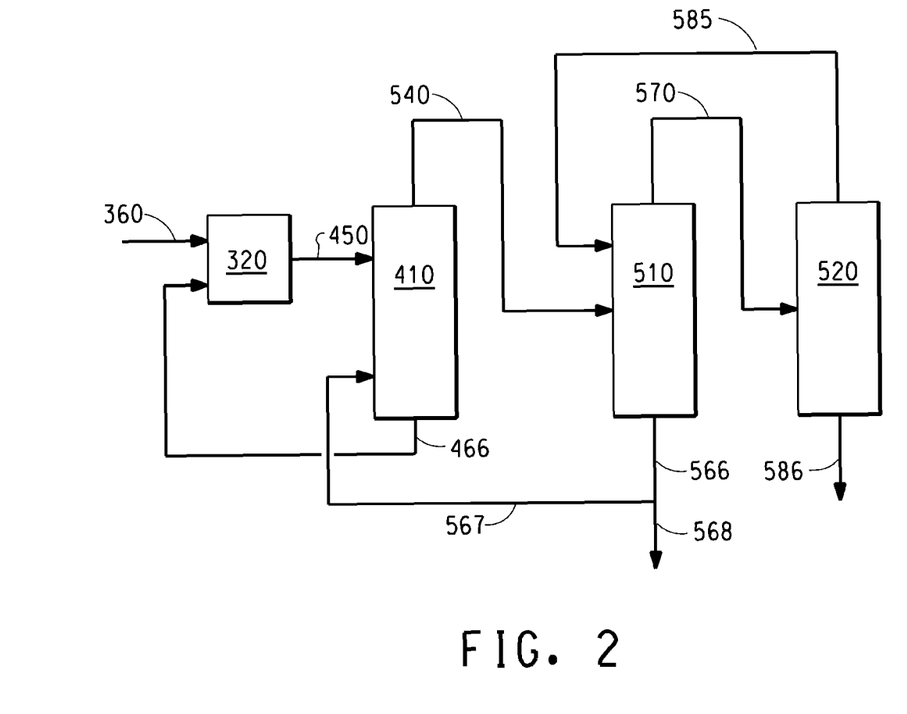
FIG. 2 illustrates one embodiment of a process to produce E-HFC-1225ye essentially free of HF and HFC-236, including distillation steps for the separation of E-HFC-1225ye from HFC-236 and from HF.

FIG. 2 is illustrative of one embodiment for practicing the present process for production of E-HFC-1225ye. HFC-236 is fed through line 360 to reactor 320. The reactor effluent mixture comprising HF, HFC-236 and E-HFC-1225ye, exits the reactor through line 450 and is fed to a multiple stage distillation column 410. The bottoms of distillation column 410, containing essentially pure HFC-236 is removed from the bottom of column 410 through line 466 and optionally may be recycled back to the reactor. The distillate from column 410, containing the HF/E-HFC-1225ye azeotrope is removed from the top of column 410 and is sent through line 540 to a second multiple stage distillation column 510. The bottoms from column 510, which is essentially pure E-HFC-1225ye, is removed from column 510 through line 566 and may be recycled back to the reactor 320 as a heat carrier through line 567 or removed from the process through line 568. The distillate from column 510, containing the HF/E-HFC-1225ye azeotrope, is fed through line 570 to a third multiple stage distillation column 520. The distillate from column 520 comprising HF/E-HFC-1225ye is removed through line 585 and may be recycled to the second distillation column 510. The bottoms composition from column 520 is essentially pure HF and is removed from column 520 through line 586. The essentially pure HF product from this process may be used in any manner appropriate such as feeding to a fluorination reactor for production of a fluorochemical compound, or may be neutralized for disposal.

Azeotropic Distillation with no Added Entraining Agent for Separation of E-HFC-1225ye and HF In another embodiment, the present invention provides a process for separating HF and E-HFC-1225ye by azeotropic distillation with and without the use of an entraining agent.

It has been unexpectedly found that E-HFC-1225ye and HF form two liquid phases when condensed and/or cooled. The two phases comprise an E-HFC-1225ye-rich phase and an HF-rich phase. This phase behavior allows unique separation schemes utilizing liquid-liquid separation (such as decantation) of the two phases that are not possible with many hydrofluorocarbons, which in general do not phase separate in the same manner.

In one embodiment, a composition comprising HF and E-HFC-1225ye may be fed to a first distillation column. The composition may contain any concentration of the two components.

In another embodiment, the composition comprising HF and E-HFC-1225ye may be fed to a condenser or cooler prior to being fed to the distillation column.

The weight ratio of the HF and E-HFC-1225ye fed to the distillation process will depend upon the means of producing the composition. In one embodiment, the HF may be from about 3 weight percent to about 85 weight percent of the composition; the E-HFC-1225ye may be from about 97 weight percent to about 15 weight percent.

In another embodiment, the HF may be from about 5 weight percent to about 50 weight percent and the E-HFC-1225ye may be from about 95 weight percent to about 50 weight percent In yet another embodiment the composition comprising HF and E-HFC-1225ye may be produced in a dehydrofluorination reactor resulting in a 50/50 mole ratio of HF to the E-HFC-1225ye.

In one embodiment, the compositions comprising HF and E-HFC-1225ye may be prepared by any convenient method to combine the desired amounts of the individual components. A preferred method is to weigh the desired component amounts and thereafter combine the components in an appropriate vessel. Agitation may be used, if desired.

Alternatively, the compositions comprising HF and E-HFC-1225ye may be prepared by feeding the effluent from a reactor, including a dehydrofluorination reactor that contains HF and E-HFC-1225ye, to the first distillation column.

In one embodiment, wherein the composition comprising HF and E-HFC-1225ye has a concentration of E-HFC-1225ye that is greater than the azeotrope concentration of E-HFC-1225ye, the first distillation column removes the excess E-HFC-1225ye from the bottom of the column and the azeotrope composition exits the top of the column as the distillate. The azeotrope composition comprising HF and E-HFC-1225ye may be condensed and cooled thereby forming two liquid phases, an HF-rich phase and an E-HFC-1225ye-rich phase. For this embodiment, the E-HFC-1225ye rich phase is recycled back to the first distillation column and the HF rich phase is fed to a second distillation column. As the HF-rich phase may have HF in excess of the azeotrope composition for HF/E-HFC-1225ye, the excess HF will be removed from the second distillation column bottom.

In another embodiment the composition comprising HF and E-HFC-1225ye has greater concentration of HF than the azeotrope composition for HF and E-HFC-1225ye. The excess HF may be removed from the bottom of the first distillation column and the azeotrope composition exits as the distillate. In a few cases, the azeotrope composition comprising HF and fluoroolefin may be condensed and cooled thereby forming two liquid phases, an HF-rich phase and an E-HFC-1225ye-rich phase. For this embodiment, the HF-rich phase is recycled back to the first distillation column and the E-HFC-1225ye-rich phase is fed to a second distillation column. As the E-HFC-1225ye-rich phase has E-HFC-1225ye in excess of the azeotrope composition for HF/E-HFC-1225ye, the excess E-HFC-1225ye may be removed from the second distillation column bottom as E-HFC-1225ye essentially free of HF.

In one embodiment the operating conditions for the first and second distillation columns will depend upon the desired purity of the E-HFC-1225ye product and the composition of the feed. In one embodiment, the first and second distillation column may operate at from about 14.7 psi (101 kPa) to about 300 psi (2068 kPa), with a top temperature of from about −50° C. to about 200° C. and a bottom temperature from about −30° C. to about 220° C. In another embodiment, the pressure will range from about 50 psi (345 kPa) to about 250 psi (1724 kPa), with a top temperature of from about −25° C. to about 100° C. and a bottom temperature from about 0° C. to about 150° C.

Figure 3:
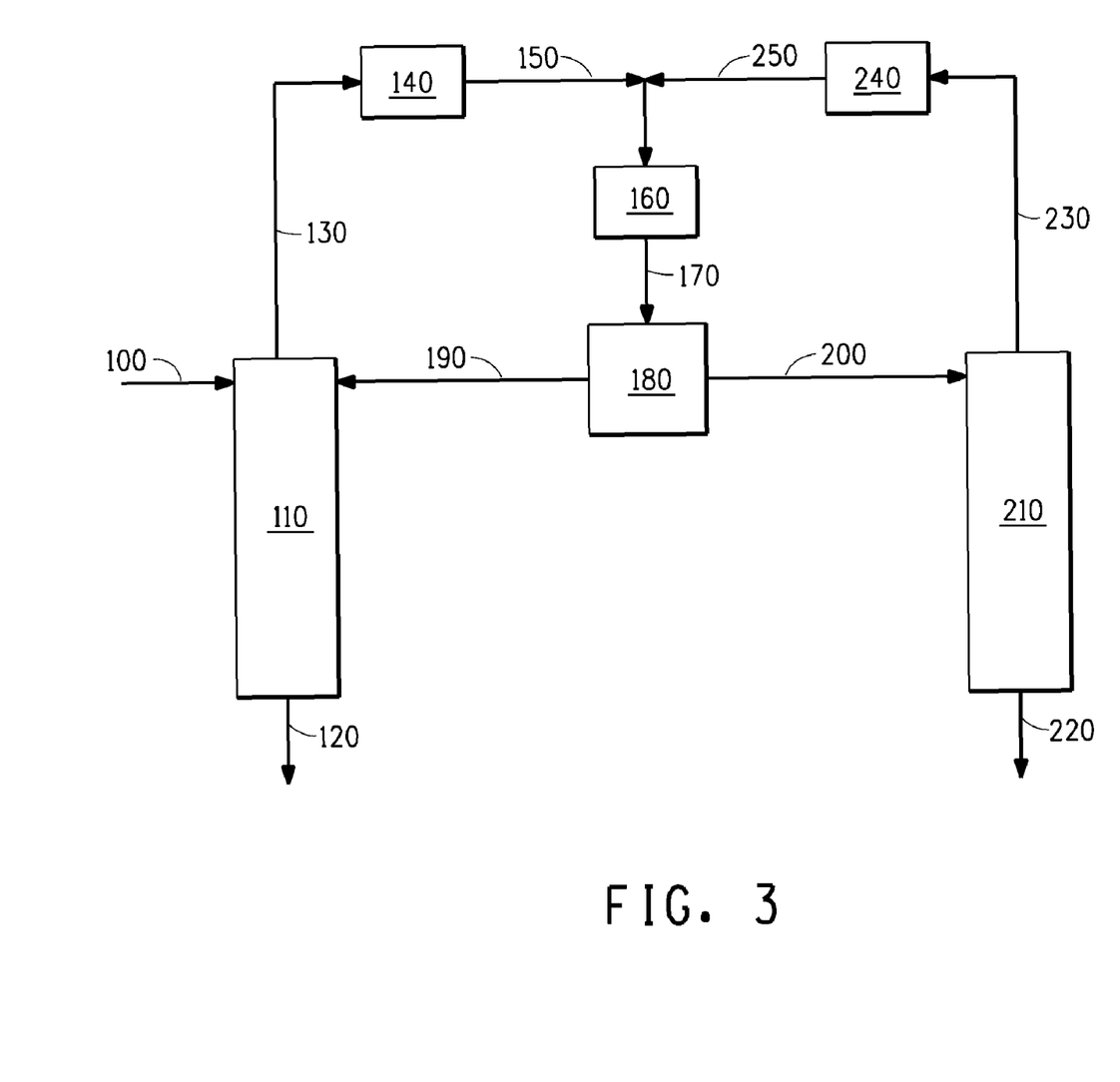
FIG. 3 illustrates one embodiment of an azeotropic distillation process with no added entraining agent for the separation of E-HFC-1225ye and HF.

Referring now to FIG. 3, one embodiment of this process is illustrated. A composition comprising HF and E-HFC-1225ye is fed to a first column 110 via stream 100. This first column is operated under appropriate conditions to approach the low-boiling HF/E-HFC-1225ye azeotrope. In one embodiment, E-HFC-1225ye is being fed to this first column in excess of that needed to form the azeotrope with the HF.

E-HFC-1225ye is recovered as the bottoms of the column via stream 120, while a composition near to the HF/E-HFC-1225ye azeotrope is recovered as distillate via stream 130. Stream 130 is condensed in 140, mixed with a nearly azeotropic composition recycled from a second column 210 via stream 250 and the combined stream is sub-cooled in cooler 160 and sent to decanter 180 where the combined stream 170 separates into separate E-HFC-1225ye-rich (190) and HF-rich (200) streams. Stream 190 is recycled to the first column as reflux. Stream 200 is fed to the top stage of the second distillation column 210, operated under conditions to approach the HF/E-HFC-1225ye azeotrope. Because the HF is being fed to this second column in excess of that needed to form the low-boiling HF/E-HFC-1225ye azeotrope, HF is recovered as the bottoms of the column via stream 220 while a composition close to the HF/E-HFC-1225ye azeotrope is recovered as distillate via stream 230. Stream 230 is condensed in 240, mixed with the nearly azeotropic composition from the first column via stream 150 and fed to cooler 160 and then decanter 180.

In another embodiment, still referring to FIG. 3, HF is being fed to this first column in excess of that needed to form the azeotrope with the HF. HF is recovered as the bottoms of the column via stream 120, while a composition near to the HF/E-HFC-1225ye azeotrope is recovered as distillate via stream 130. Stream 130 is condensed in 140, mixed with a nearly azeotropic composition recycled from a second column 210 via stream 250 and the combined stream is sub-cooled in cooler 160 and sent to decanter 180 where the combined stream 170 separates into separate E-HFC-1225ye-rich (200) and HF-rich (190) streams. Stream 200 is recycled to the first column as reflux. Stream 190 is fed to the top stage of the second distillation column 210, operated under conditions to approach the HF/E-HFC-1225ye azeotrope. Because the E-HFC-1225ye is being fed to this second column in excess of that needed to form the low-boiling HF/E-HFC-1225ye azeotrope, E-HFC-1225ye is recovered as the bottoms of the column via stream 220 while a composition close to the HF/E-HFC-1225ye azeotrope is recovered as distillate via stream 230. Stream 230 is condensed in 240, mixed with the nearly azeotropic composition from the first column via stream 150 and fed to cooler 160 and then decanter 180.

In yet another embodiment, still referring to FIG. 3, the initial feed of the composition comprising HF and E-HFC-1225ye may be to a different piece of equipment. Rather than being fed to a distillation column, the composition may be fed to the cooler 160 or a condenser (140 or 240). In another embodiment, the two columns share a single condenser (not shown in a figure) and the distillate compositions from both columns (130 and 230) are both fed to that common condenser prior to feeding to the cooler 160 and decanter 180.

Azeotropic Distillation with an Entraining Agent for Separation of E-HFC-1225ye and HF Azeotropic distillation for separating E-HFC-1225ye from mixtures of HF and E-HFC-1225ye may in another embodiment be carried out using an entraining agent compound. For the process including an entraining agent, the azeotrope composition need not phase separate upon condensing and cooling as described above.

The present invention further provides a process for separating E-HFC-1225ye from a mixture comprising hydrogen fluoride and E-HFC-1225ye, said process comprising:
 a. contacting a first composition comprising E-HFC-1225ye and hydrogen fluoride with an entraining agent to form a second composition;
 b. distilling the second composition thereby separating E-HFC-1225ye from hydrogen fluoride and entraining agent; and
 c. recovering E-HFC-1225ye product essentially free of hydrogen fluoride.

Azeotropic distillation for separating E-HFC-1225ye from mixtures of HF and E-HFC-1225ye may, in another embodiment, be carried out using an entraining agent compound. For the process including an entraining agent, the azeotrope composition need not phase separate upon condensing and cooling as described above.

In one embodiment, the entraining agent serves to provide an improved liquid-liquid phase separation for a system wherein that separation would otherwise not be effective.

In one embodiment, the E-HFC-1225ye is present in the HF/E-HFC-1225ye mixture in a concentration greater than the azeotrope concentration for said E-HFC-1225ye and HF. Thus, in one embodiment is provided a process for the purification of a E-HFC-1225ye from a mixture comprising E-HFC-1225ye and HF, wherein said E-HFC-1225ye is present in said mixture in a concentration greater than the azeotrope concentration for said E-HFC-1225ye and HF, said process comprising:
 a. adding an entraining agent to the mixture comprising E-HFC-1225ye and HF thus forming a second mixture;
 b. distilling said second mixture in a first distillation step to form a first distillate composition comprising HF, E-HFC-1225ye, and entraining agent, and a first bottoms composition comprising E-HFC-1225ye essentially free of HF and entraining agent;
 c. condensing said first distillate composition to form two liquid phases, being i) an HF-rich phase and ii) an entraining agent-rich phase; and d. optionally recycling the entraining agent-rich phase back to the first distillation step. In another embodiment, the process further comprises feeding the HF-rich phase to a second distillation step and forming a second distillate composition comprising entraining agent, E-HFC-1225ye and HF and a bottoms composition comprising HF essentially free of E-HFC-1225ye and entraining agent. In another embodiment, the process may further comprise recycling said second distillate composition back to the two liquid phases.

The process for separating a E-HFC-1225ye from a first composition comprising HF and E-HFC-1225ye comprises contacting said first composition with an entraining agent to form a second composition. The contacting may occur in a first distillation column, or the second composition may be formed by mixing the components prior to feeding to a distillation column in a pre-mixing step.

The weight ratio of the HF and E-HFC-1225ye in the first composition will depend upon the means of producing the composition. In one embodiment, the HF may be from about 3 weight percent to about 85 weight percent of the composition; the E-HFC-1225ye may be from about 97 weight percent to about 15 weight percent.

In another embodiment, the HF may be from about 5 weight percent to about 50 weight percent and the E-HFC-1225ye may be from about 95 weight percent to about 50 weight percent In yet another embodiment the composition comprising HF and E-HFC-1225ye may be produced in a dehydrofluorination reactor resulting in a 50/50 mole ratio of HF to the E-HFC-1225ye.

In one embodiment, the compositions comprising HF and E-HFC-1225ye may be prepared by any convenient method to combine the desired amounts of the individual components. A preferred method is to weigh the desired component amounts and thereafter combine the components in an appropriate vessel. Agitation may be used, if desired.

Alternatively, the compositions comprising HF and E-HFC-1225ye may be prepared by feeding the effluent from a reactor, including a dehydrofluorination reactor that contains HF and E-HFC-1225ye, to the first distillation column. The entraining agent may be added at a separate feed point such that the second composition is formed directly in the distillation column. Alternatively, the entraining agent may be mixed with the first composition comprising HF and E-HFC-1225ye thus forming the second composition prior to the distillation column in a pre-mixing step.

In one embodiment of the separation process, a composition comprising E-HFC-1225ye and HF is fed directly to a first distillation column. In another embodiment, the E-HFC-1225ye and HF may be pre-mixed with an entraining agent prior to the distillation column. The pre-mixing step may occur in a cooler (160 in FIG. 4). Then the cooled mixture is fed to a decanter (180 in FIG. 4) prior to feeding to the distillation column.

In one embodiment, the first distillate composition comprises a low boiling azeotrope of HF and entraining agent optionally containing minor amounts of E-HFC-1225ye. Further, in another embodiment, the E-HFC-1225ye essentially free of HF and optionally minor amounts of entraining agent may be recovered from the bottom of the first distillation column.

The operating variables for the first distillation column will depend strongly on the entraining agent being used in the separation process. In general the first distillation column may operate at pressures from about 14.7 psi (101 kPa) to about 500 psi (3448 kPa) with a top temperature of from about −50° C. to about 100° C. and a bottom temperature of from about −30° C. to about 200° C. In another embodiment, the first distillation column will operate at pressures from about 100 psi (690 kPa) to about 400 psi (2758 kPa) with a top temperature of from about −50° C. to about 50° C. and a bottom temperature from about 10° C. to about 150° C.

It was surprisingly calculated that in some few cases, azeotropes of HF and compounds used as entraining agents will separate into HF-rich and entraining agent-rich liquid fractions upon condensing and being cooled. In one embodiment, the first distillate composition may be fed to a liquid separation zone (e.g. decanter). The first distillate composition comprising an azeotrope of HF and entraining agent may be phase separated forming two liquid phases, one being HF-rich and the other being entraining agent-rich. The lower density phase may be recovered from the top of the liquid separation zone and the higher density phase may be recovered from the bottom of the liquid separation zone. The entraining agent-rich phase (whether higher or lower density) may be fed back to the first distillation column. In one embodiment the HF-rich phase may be fed to a second distillation column or in another embodiment, the HF-rich phase may be split to send some portion back to the first distillation column (in order to provide more reflux and allow the first distillation column to operate properly) and the remainder may be fed to the second distillation column. The second distillation column allows recovery of HF essentially free of E-HFC-1225ye and entraining agent as a bottoms composition. The top composition comprising E-HFC-1225ye, HF and entraining agent may be recycled to the liquid separation zone, be utilized in some other manner, or disposed. The operating variables for the second distillation column will depend strongly on the entraining agent being used in the separation process. In general the second distillation column may operate at pressures from about 14.7 psi (101 kPa) to about 500 psi (3448 kPa) with a top temperature of from about −50° C. to about 100° C. and a bottom temperature of from about −30° C. to about 200° C. In another embodiment, the first distillation column will operate at pressures from about 100 psi (690 kPa) to about 400 psi (2758 kPa) with a top temperature of from about −25° C. to about 50° C. and a bottom temperature from about zero ° C. to about 150° C.

Figure 4:
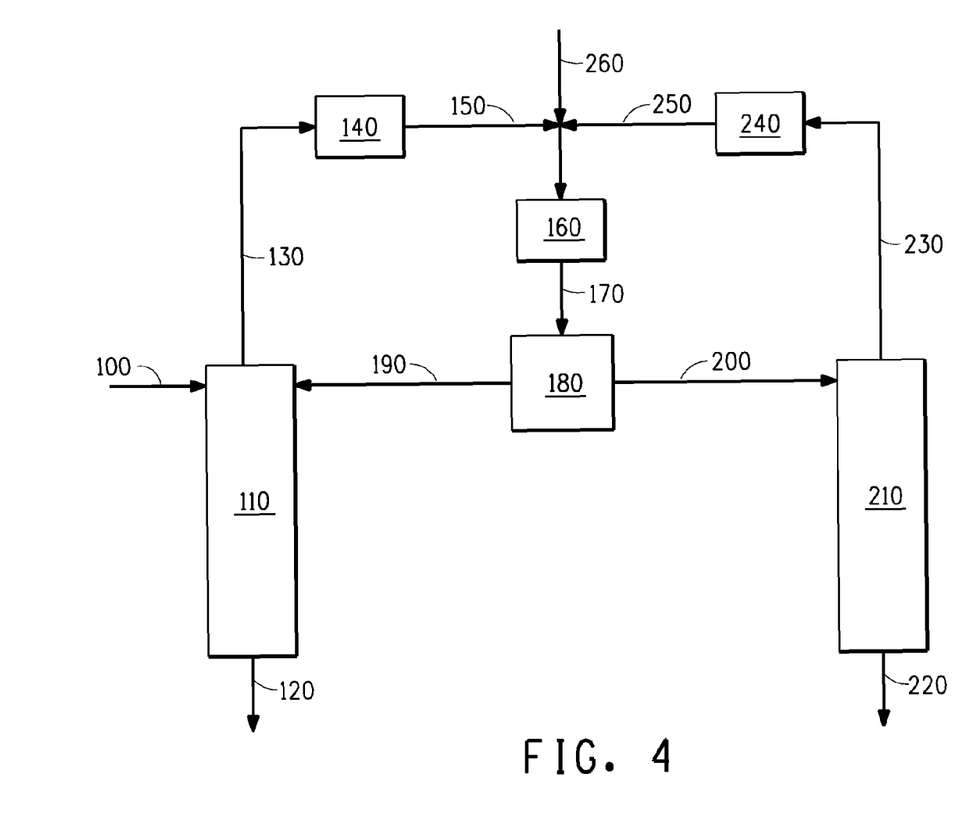
FIG. 4 illustrates one embodiment of an azeotropic distillation process with an added entraining agent for the separation of E-HFC-1225ye and HF.

Referring now to FIG. 4, a composition comprising HF and E-HFC-1225ye is fed to a first distillation column 110 via stream 100. An entraining agent-rich composition is also fed to the top stage of column 110 via stream 190. If the combined amount of E-HFC-1225ye in streams 100 and 190 is in excess of that needed to form the low-boiling HF/E-HFC-1225ye azeotrope, E-HFC-1225ye is recovered essentially free of both HF and entraining agent from the bottom of column 110 via stream 120. A ternary composition comprising HF, E-HFC-1225ye, and entraining agent, but enriched in E-HFC-1225ye relative to stream 190, leaves the top of the first column as the first distillate stream 130. Stream 130 is condensed by condenser 140 forming stream 150 and mixed with a condensed second distillate stream 250 from a second distillation column. In one embodiment, additional entraining agent may be added via stream 260, if needed. Combined streams 150, 250, and 260 are fed to cooler 160 and then to decanter 180 where the sub-cooled liquid stream 170 separates into entraining agent-rich and HF-rich liquid phase compositions which leave the decanter via streams 190 and 200, respectively. The E-HFC-1225ye present distributes between the two liquid phases with the majority ending up in the entraining agent-rich phase. The HF-rich composition stream 200 is fed to the top stage of the second distillation column 210.

Because the amount of HF in stream 200 is in excess of that needed to form a low-boiling HF/E-HFC-1225ye azeotrope, HF is recovered as a product stream essentially free of both E-HFC-1225ye and entraining agent from the bottom of column 210 via stream 220. A ternary composition comprising HF, E-HFC-1225ye and entraining agent, but enriched in entraining agent relative to stream 200, leaves the top of the second column as the second distillate stream 230. Stream 230 is condensed in condenser 240, forming stream 250, and combined with streams 150 and 260 previously described.

Alternatively, in another embodiment, rather than feed the HF/E-HFC-1225ye mixture directly to the distillation column 110, the mixture may be fed to cooler 160 and then to decanter 180 where the mixture phase separates. Then stream 190 carries the mixture of HF, E-HFC-1225ye and entraining agent to the first distillation column 110.

In another embodiment, the concentration of HF in the HF/E-HFC-1225ye mixture is greater than the concentration in the azeotrope of E-HFC-1225ye and HF. Thus, in another embodiment is provided a process for the purification of HF from a mixture comprising a E-HFC-1225ye and HF, wherein HF is present in a concentration greater than the azeotrope concentration for HF and said E-HFC-1225ye, said process comprising:

a. adding an entraining agent to the mixture comprising E-HFC-1225ye and HF thus forming a second mixture;
b. distilling said second mixture in a first distillation step to form a first distillate composition comprising HF, entraining agent, and a E-HFC-1225ye, and a first bottoms composition comprising HF essentially free of E-HFC-1225ye and entraining agent;
c. condensing said first distillate composition to form two liquid phases, being i) an entraining agent-rich phase and ii) an HF-rich phase; and
d. optionally recycling the HF-rich phase back to the first distillation step. In another embodiment, the process may further comprising feeding the HF-rich phase to a second distillation step and forming a second distillate composition comprising entraining agent, HF, and E-HFC-1225ye, and a bottoms composition comprising E-HFC-1225ye essentially free of entraining agent. In another embodiment, the process may further comprise recycling said second distillate composition back to the two liquid phases.

Referring again to FIG. 4, a composition comprising HF and E-HFC-1225ye is fed to a first distillation column 110 via stream 100. An HF-rich composition is also fed to the top stage of column 110 via stream 190. If the combined amount of HF in streams 100 and 190 is in excess of that needed to form the low-boiling HF/E-HFC-1225ye azeotrope, HF is recovered essentially free of both E-HFC-1225ye and entraining agent from the bottom of column 110 via stream 120. A composition near the HF/E-HFC-1225ye azeotrope with a minor amount of entraining agent is recovered as the first distillate via stream 130. Stream 130 is condensed by condenser 140 forming stream 150 and mixed with a condensed second distillate stream 250 from a second distillation column. In one embodiment, additional entraining agent may be added via stream 260, if needed. Combined streams 150, 250, and 260 are fed to cooler 160 and then to decanter 180 where the sub-cooled liquid stream 170 separates into HF-rich and entraining agent-rich liquid phase compositions which leave the decanter via streams 190 and 200, respectively. The E-HFC-1225ye present distributes between the two liquid phases with the majority ending up in the entraining agent-rich phase. The entraining agent-rich composition stream 200 is fed to the top stage of the second distillation column 210. Because the amount of E-HFC-1225ye in stream 200 is in excess of that needed to form a low-boiling entraining agent/E-HFC-1225ye azeotrope, E-HFC-1225ye is recovered as a product stream essentially free of both HF and entraining agent from the bottom of column 210 via stream 220. A ternary composition comprising entraining agent, E-HFC-1225ye, and HF, but enriched in entraining agent relative to stream 200 leaves the top of the second column as the second distillate stream 230. Stream 230 is condensed in condenser 240, forming stream 250, and combined with streams 150 and 260 previously described.

Alternatively, in another embodiment, rather than feed the HF/E-HFC-1225ye mixture directly to the distillation column 110, the mixture may be fed to cooler 160 and then to decanter 180 where the mixture phase separates. Then stream 190 carries the mixture of HF, E-HFC-1225ye and entraining agent as the HF-rich phase to the first distillation column 110.

Extractive Distillation to Separate E-HFC-1225ye and Z-HFC-1225ye

The measured normal boiling points of HFC-Z-1225ye and HFC-E-1225ye are $-19.41°$ C. and $-14.99°$ C., respectively. The closeness of the boiling points suggests that the relative volatility of the two isomers will be low, making isomer separation by ordinary fractional distillation difficult. This is confirmed by calculated relative volatility values between 1.17 and 1.20 for various mixtures of the two isomers at $-10°$ C.

According to the present invention, there is provided a process for separating E-1,1,1,2,3-pentafluoropropene (E-HFC-1225ye) from a first mixture comprising E-1,1,1,2,3-pentafluoropropene (E-HFC-1225ye) and Z-1,1,1,2,3-pentafluoropropene (Z-HFC-1225ye) by using extractive agents. The process comprises the steps of (a) contacting the first mixture with at least one extractive agent to form a second mixture, (b) distilling the second mixture, and (c) recovering E-1,1,1,2,3-pentafluoropropene (E-HFC-1225ye) essentially free of Z-1,1,1,2,3-pentafluoropropene (Z-HFC-1225ye).

Figure 5:
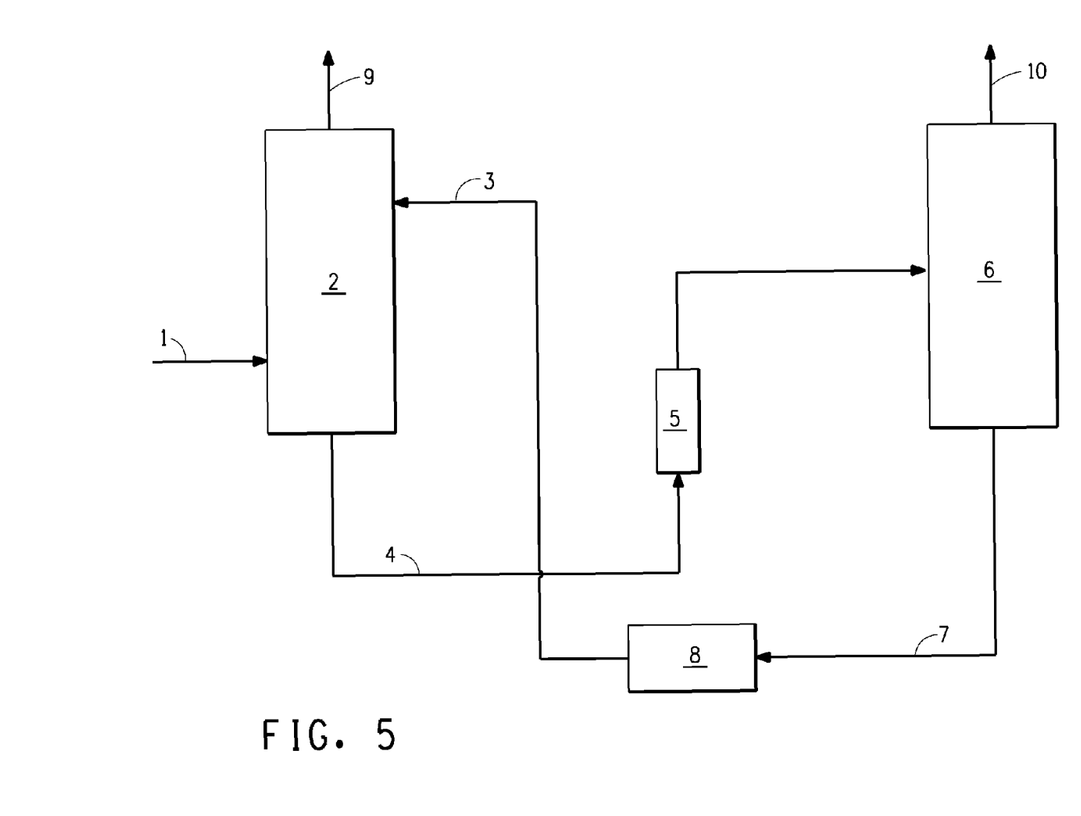
FIG. 5 illustrates one embodiment of an extractive distillation for the separation of E-HFC-1225ye and Z-HFC-1225ye using an extractive agent.

The present inventive process can be better understood by reference to FIG. 5, which illustrates a system, which can be used for performing the embodiments of the present extractive distillation process wherein E-HFC-1225ye is separated from a first mixture comprising E-HFC-1225ye and Z-HFC-1225ye using at least one extractive agent.

Referring now to FIG. 5, a first mixture comprising E-HFC-1225ye and Z-HFC-1225ye impurity is supplied via conduit 1 to extraction column 2. At least one extractive agent is supplied via conduit 3 to the extraction column 2 at a feed point higher in the column than the feed point of the first mixture. A stream comprising the extractive agent and E-HFC-1225ye essentially free of Z-HFC-1225ye is removed from the bottom of column 2 via conduit 4 and transported to optional cooler 5 and from there fed to stripping column 6. The overhead distillate from column 2 contains concentrated Z-HFC-1225ye impurity. Stripping column 6 separates the extractive agent from E-HFC-1225ye. Extractive agent is removed from the bottom of column 6 via conduit 7 and transported to optional cooler 8 and from there returned to extraction column 2 as extractive agent feed. The overhead distillate from column 6 contains E-HFC-1225ye essentially free of Z-HFC-1225ye and the extractive agent.

In one embodiment of the invention, extractive agents suitable for separation of E-HFC-1225ye from Z-HFC-1225ye are compounds having a normal boiling point between $-10°$ C. and $120°$ C.

In another embodiment of the invention, extractive agents are compounds having a normal boiling point between $10°$ C. and $100°$ C.

In yet another embodiment of the invention, extractive agents are compounds having a normal boiling point between 30° C. and 70° C.

Normal boiling point is the boiling temperature of a liquid at which vapor pressure is equal to one atmosphere.

These extractive agents may be used alone or in combination with each other as the extractive agents for the separation.

In one embodiment of this invention, Z-HFC-1225ye becomes more volatile than E-HFC-1225ye in the presence of the extractive agent, and is removed from the top of the distillation column. E-HFC-1225ye is recovered as a bottoms product together with extractive agent, and is further separated from the extractive agent in a conventional distillation column.

In another embodiment of this invention, E-HFC-1225ye becomes more volatile than Z-HFC-1225ye in the presence of the extractive agent, and is recovered as pure product from the top of the distillation column. Z-HFC-1225ye is removed from the bottom of the distillation column together with extractive agent.

In the extractive distillation process, the extractive agent is preferably recycled. For instance, for extractive agents causing Z-HFC-1225ye to become more volatile than E-HFC-1225ye, extractive agent will be recovered from the bottom of the extraction column together with E-HFC-1225ye, and may optionally be further purified in a conventional distillation column and recycled to the contacting step.

In one embodiment of this invention, the first mixture comprises more than about 70 weight percent Z-HFC-1225ye and less than about 30 weight percent E-HFC-1225ye.

In another embodiment of this invention, the first mixture comprises more than about 85 weight percent of Z-HFC-1225ye and less than about 15 weight percent E-HFC-1225ye.

In another embodiment of this invention, the first mixture comprises more than about 98 weight percent of Z-HFC-1225ye and less than about 2 weight percent E-HFC-1225ye.

According to the present invention, E-1,1,1,2,3-pentafluoropropene (E-HFC-1225ye) containing less than 100 ppm of Z-1,1,1,2,3-pentafluoropropene (Z-HFC-1225ye) may be produced. Further, E-1,1,1,2,3-pentafluoropropene (E-HFC-1225ye) containing less than 10 ppm of Z-1,1,1,2,3-pentafluoropropene (Z-HFC-1225ye), and even further E-1,1,1,2,3-pentafluoropropene (E-HFC-1225ye) containing less than 1 ppm of Z-1,1,1,2,3-pentafluoropropene (Z-HFC-1225zc) may be produced.

Alternatively, in another embodiment, Z-1,1,1,2,3-pentafluoropropene (Z-HFC-1225ye) containing less than 100 ppm of E-1,1,1,2,3-pentafluoropropene (E-HFC-1225ye) may be produced. Further, Z-1,1,1,2,3-pentafluoropropene (Z-HFC-1225ye) containing less than 10 ppm of E-1,1,1,2,3-pentafluoropropene (E-HFC-1225ye), and even further Z-1,1,1,2,3-pentafluoropropene (Z-HFC-1225ye) containing less than 1 ppm of E-1,1,1,2,3-pentafluoropropene (E-HFC-1225zc) may be produced.

Also according to the present invention, Z-1,1,1,2,3-pentafluoropropene (Z-HFC-1225ye) containing less than 100 ppm of impurities may be produced. Further, Z-1,1,1,2,3-pentafluoropropene (Z-HFC-1225ye) containing less than 10 ppm of impurities may be produced, and even further, Z-1,1,1,2,3-pentafluoropropene (Z-HFC-1225ye) containing less than 1 ppm of impurities may be produced.

In another embodiment, according to the present invention, E-1,1,1,2,3-pentafluoropropene (E-HFC-1225ye) containing less than 100 ppm of impurities may be produced. Further, E-1,1,1,2,3-pentafluoropropene (E-HFC-1225ye) containing less than 10 ppm of impurities may be produced, and even further, E-1,1,1,2,3-pentafluoropropene (E-HFC-1225ye) containing less than 1 ppm of impurities may be produced.

The ratio of the material exiting the top of the extractive distillation column, which is then condensed and in turn returned to the column, to the amount of remainder material that is removed or recovered is commonly referred to as the reflux ratio. The reflux ratio will define the physical characteristics of the extractive distillation column. For example, when THF or methanol is used as the extractive agent, an increase in the reflux ratio will in turn cause an increase in the E-HFC-1225ye recovery efficiency by reducing the quantity of E-HFC-1225ye in the overhead stream.

While not illustrated in the figures, it is understood that certain pieces of process equipment may be used in the processes described herein, for optimization. For instance, pumps, heaters or coolers may be used where appropriate. As an example, it is desirable to have the feed to a distillation column at the same temperature as the point in the column to which it is fed. Therefore, heating or cooling of the process stream may be necessary to match the temperature.

Without further elaboration, it is believed that one skilled in the art can, using the description herein, utilize the disclosed compositions and processes to their fullest extent. The following exemplary embodiments are, therefore, to be construed as merely illustrative, and do not constrain the remainder of the disclosure in any way whatsoever.

EXAMPLES

Example 1

Dehydrofluorination of HFC-236ea to HFC-1225ye (E and Z Isomers) Over Carbonaceous Catalyst To a Hastelloy nickel alloy reactor (1.0" OD×0.854" ID×9.5" L) was charged 14.32 g (25 mL) of spherical (8 mesh) three dimensional matrix porous carbonaceous material prepared substantially as described in U.S. Pat. No. 4,978,649, incorporated herein by reference. The packed portion of the reactor was heated by a 5"×1" ceramic band heater clamped to the outside of the reactor. A thermocouple, positioned between the reactor wall and the heater measured the reactor temperature. After charging the reactor with the carbonaceous material, nitrogen (10 mL/min) was passed through the reactor and the temperature was raised to 200° C. during a period of one hour and maintained at this temperature for an additional 4 hours. The reactor temperature was then raised to the desired operating temperature and a flow of HFC-236ea and nitrogen was started through the reactor.

A portion of the total reactor effluent was sampled on-line for organic product analysis using a gas chromatograph equipped with a mass selective detector (GC-MS). The bulk of the reactor effluent containing organic products and also inorganic acid, such as HF, was treated with aqueous caustic for neutralization.

The results obtained in GC mole percent are summarized in Table 1.

TABLE 1

| Reactor Temp. (° C.) | 236ea feed (mL/min) | N₂ feed (mL/min) | Mole Percent | | | |
|---|---|---|---|---|---|---|
| | | | Z-1225ye | E-1225ye | 236ea | Unknowns |
| 200 | 10 | 20 | 0.03 | ND | 99.97 | ND |
| 250 | 10 | 20 | 0.2 | 0.03 | 99.8 | ND |
| 300 | 10 | 20 | 1.4 | 0.22 | 98.4 | 0.01 |
| 350 | 10 | 20 | 5.4 | 0.96 | 93.1 | 0.5 |
| 400 | 10 | 20 | 38.1 | 9.0 | 51.7 | 1.1 |
| 400 | 10 | 10 | 37.9 | 8.7 | 51.6 | 1.8 |
| 400 | 10 | 5 | 42.6 | 9.5 | 46.7 | 1.2 |
| 400 | 10 | 40 | 13.2 | 2.5 | 71.6 | 12.7 |

ND = not detected

Example 2

Phase Studies of Mixtures of HF and E-HFC-1225ye

A phase study was performed for a composition consisting essentially of E-HFC-1225ye and HF, wherein the composition is varied and the vapor pressures may be measured at both about 19.5° C. Based upon the measurements, azeotrope compositions at other temperature and pressures have been calculated.

Table 2 provides a compilation of calculated azeotrope compositions for HF and E-HFC-1225ye at specified temperatures and pressures.

TABLE 2

| Temperature, ° C. | Pressure, psi (kPa) | Mole % HF | Mole % E-HFC-1225ye |
|---|---|---|---|
| −50 | 2.71 (18.7) | 39.8 | 60.2 |
| −40 | 4.88 (33.6) | 38.2 | 61.7 |
| −30 | 8.31 (57.3) | 37.1 | 62.9 |
| −20 | 13.5 (93.1) | 37.7 | 62.3 |
| −10 | 20.9 (144) | 37.5 | 62.5 |
| 0 | 31.2 (215) | 37.4 | 62.6 |
| 10 | 45.2 (312) | 37.4 | 62.6 |
| 19.5 | 62.6 (432) | 37.4 | 62.5 |
| 30 | 87.5 (603) | 37.6 | 62.4 |
| 40 | 117 (814) | 37.7 | 62.3 |
| 50 | 154 (1069) | 38.1 | 61.9 |
| 60 | 200 (1379) | 38.7 | 61.3 |
| 70 | 255 (1758) | 39.2 | 60.8 |
| 80 | 318 (2193) | 39.6 | 60.4 |

TABLE 2-continued

| Temperature, ° C. | Pressure, psi (kPa) | Mole % HF | Mole % E-HFC-1225ye |
|---|---|---|---|
| 90 | 389 (2682) | 39.8 | 60.2 |
| 100 | 466 (3213) | 39.7 | 60.3 |
| 120 | 613 (4226) | 38.5 | 61.5 |

Example 3

Dew Point and Bubble Point Vapor Pressures

The dew point and bubble point vapor pressures for compositions disclosed herein were calculated from measured thermodynamic properties. The near-azeotrope range is indicated by the minimum and maximum concentration of E-HFC-1225ye (mole percent, mol %) for which the difference in dew point and bubble point pressures is less than or equal to 3% (based upon bubble point pressure). The results are summarized in Table 3.

TABLE 3

| Temp, ° C. | Azeotrope composition, mol % E-HFC-1225ye | Near azeotrope compositions, mol % E-HFC-1225ye | |
|---|---|---|---|
| | | Minimum | Maximum |
| −40 | 61.7 | 54.7 | 71.0 |
| 0 | 62.6 | 56.6 | 71.5 |
| 40 | 62.3 | 57.3 | 71.1 |
| 80 | 60.4 | 56.1 | 75.2 |
| 120 | 61.5 | 49.8 | 100 |

Example 4

Pressure Swing Distillation for Separation of E-HFC-1225ye from HF

Example 4 demonstrates one embodiment of the separation of E-HFC-1225ye from HF by pressure swing distillation. A mixture of HF and E-HFC-1225ye is fed to a distillation. For this example, referring to FIG. 1, the column 510 contains 20 theoretical stages with both feeds (540 and 585) being fed at the third stage from the top. Column 510 operates with a molar reflux ratio of 0.015. Column 520 contains 10 theoretical stages and the feed (570) enters on the second stage from the top. Column 520 operates with a molar reflux ratio of 0.01. The data in Table 4 were obtained by calculation using measured and calculated thermodynamic properties.

TABLE 4

| Compound or variable | 540 Feed Mixture | 570 Column 510 distillate | 566 E-HFC-1225ye product | 585 Column 520 distillate | 586 HF product |
|---|---|---|---|---|---|
| HF, mol % | 37.0 | 39.15 | 1 ppm | 37.57 | 100.0 |
| E-HFC-1225ye, mol % | 63.0 | 60.85 | 100.0 | 62.43 | <1 ppm |
| Temp., ° C. | 50.0 | 79.5 | 89.2 | −15.2 | 23.0 |
| Pres., psi (kPa) | 325 (2239) | 315 (2170) | 315 (2170) | 17 (115) | 17 (115) |

Example 5

Azeotropic Distillation for the Separation of E-HFC-1225ye and HF

Example 5 demonstrates an azeotropic distillation with no added entraining agent for the separation of E-HFC-1225ye and HF. A mixture of E-HFC-1225ye and HF is fed to a distillation column. Referring to FIG. 3, column 110 contains 15 theoretical stages with the feeds entering on the top stage and operates with a top pressure of 140 psig. Column 210 contains 10 theoretical stages and operates with a top pressure of 140 psig. The data in Table 5 were obtained by calculation using measured and calculated thermodynamic properties.

TABLE 5

| Component or variable | 100 Feed | 120 Column 110 bottom | 130 Column 110 distillate | 190 E-HFC-1225ye-rich phase | 200 HF-rich phase | 220 Column 210 bottom | 230 Column 210 distillate |
|---|---|---|---|---|---|---|---|
| E-HFC-1225ye, mol % | 63.0 | 100.0 | 62.2 | 91.9 | 18.1 | 2 ppm | 58.9 |
| HF, mol % | 37.0 | 7 ppm | 37.8 | 8.1 | 81.9 | 100.0 | 41.1 |
| Temp., °C. | 30.0 | 57.8 | 49.9 | −40.0 | −40.0 | 100.9 | 50.3 |
| Pres., psi (kPa) | 164.7 (1136) | 154.7 (1067) | 154.7 (1067) | 154.6 (1066) | 154.6 (1066) | 154.7 (1067) | 154.6 (1066) |

Example 6

Extractive Distillation for the Separation of E-HFC-1225ye from Z-HFC-1225ye Example 6 demonstrates a separation of E-HFC-1225ye from Z-HFC-1225ye by extractive distillation using tetrahydrofuran (THF) as the extractive agent.

Referring to FIG. 5, a mixture of Z-HFC-1225ye and E-HFC-1225ye is fed to the 24th stage from the top of distillation column 2 with 46 theoretical stages; operating with a top pressure of 35 psi and a reflux ratio of 4.0. THF is fed to the 7th stage from the top of column 2 via stream 3 to serve as the extractive agent for the separation. The flow rate of stream 3 is adjusted to be 30 times the flow rate of stream 1 on a molar basis (16.4 on a mass basis). Distillation column 6 contains 25 theoretical stages with the feed entering at the 9th stage from the top and operates with reflux ratio of 3.2 and a top pressure of 15 psi. The data in Table 6 were obtained by calculation using measured and calculated thermodynamic properties.

TABLE 6

| Component or variable | 1 Column 2 feed | 4 Column 2 bottom | 9 Column 2 distillate | 7 Column 6 bottom | 10 Column 6 distillate |
|---|---|---|---|---|---|
| E-HFC-1225ye, mol % | 3.8 | 0.13 | 0.05 | <1 ppm | 79.5 |
| Z-HFC-1225ye, mol % | 96.2 | 0.03 | 99.95 | <1 ppm | 20.5 |
| THF, mol % | 0 | 99.8 | <1 ppm | 100.0 | <1 ppm |
| Temp., °C. | 10.0 | 110.5 | 12.5 | 90.7 | 1.6 |
| Pres., psia (kPa) | 51.8 (357) | 51.8 (357) | 49.7 (343) | 30.8 (212) | 29.7 (205) |

The foregoing description is exemplary and explanatory only and is not intended to be restrictive of the invention, as defined in the appended claims.

What is claimed is:

1. An azeotrope or near-azeotrope composition comprising from about 57.0 mole percent to about 78.0 mole percent E-HFC-1225ye and from about 43.0 mole percent to about 22.0 mole percent hydrogen fluoride.

2. The azeotrope or near-azeotrope composition of claim 1 comprising from about 57.0 mole percent to about 78.0 mole percent E-HFC-1225ye and from about 43.0 mole percent to about 22.0 mole percent hydrogen fluoride, wherein the vapor pressure is from about 2.0 psi (13.8 kPa) to about 477 psi (3289 kPa) at a temperature of from about −50° C. to about 100° C.

3. The azeotrope composition of claim 1 comprising from about 61.9 mole percent to about 69.2 mole percent E-HFC-1225ye and from about 38.1 mole percent to about 30.8 mole percent hydrogen fluoride, wherein the vapor pressure is from about 2.0 psi (13.8 kPa) to about 477 psi (3289 kPa) at a temperature of from about −50° C. to about 100° C.

4. The azeotrope or near-azeotrope composition of claim 1, wherein said composition is characterized by a difference between dew point pressure and bubble point pressure that is less than or equal to 3%, based upon bubble point pressure.

5. A process for the separation of E-HFC-1225ye from HFC-236 comprising:
   a. forming a mixture of E-HFC-1225ye, HFC-236, and hydrogen fluoride; and
   b. subjecting said mixture to a distillation step forming a column distillate composition comprising an azeotrope or near-azeotrope composition of hydrogen fluoride and E-HFC-1225ye essentially free of HFC-236;
   wherein said azeotrope or near-azeotrope composition comprises from about 57.0 mole percent to about 78.0 mole percent E-HFC-1225ye and from about 43.0 mole percent to about 22.0 mole percent hydrogen fluoride.

6. The process of claim 5 wherein said column-bottoms composition comprises HFC-236 essentially free of hydrogen fluoride.

7. A process for the purification of E-HFC-1225ye from a mixture of E-HFC-1225ye, HFC-236, and hydrogen fluoride, said process comprising:
   a. subjecting said mixture to a first distillation step to form a first distillate comprising an azeotrope or near-azeotrope composition containing E-HFC-1225ye and hydrogen fluoride and a first bottoms comprising HFC-236;
   b. subjecting said first distillate to a second distillation step from which a composition enriched in either (i) hydrogen fluoride or (ii) E-HFC-1225ye is removed as a second distillate composition with a second bottoms composition being enriched in the other of said components (i) or (ii); and
   c. subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition; wherein said azeotrope or near-azeotrope composition of (a) comprises from about 57.0 mole percent to about 78.0 mole percent E-HFC-1225ye and from about 43.0 mole percent to about 22.0 mole percent hydrogen fluoride.

8. A process to produce E-HFC-1225ye essentially free of HF and HFC-236 comprising:
   a. feeding HFC-236 to a reaction zone for dehydrofluorination to form a reaction product composition comprising E-HFC-1225ye, unreacted HFC-236 and hydrogen fluoride;
   b. subjecting said reaction product composition to a first distillation step to form a first distillate composition comprising an azeotrope or near-azeotrope composition containing E-HFC-1225ye and hydrogen fluoride and a first bottoms composition comprising HFC-236;
   c. subjecting said first distillate composition to a second distillation step from which a composition enriched in either (i) hydrogen fluoride or (ii) E-HFC-1225ye is removed as a second distillate composition with a second bottoms composition being enriched in the other of said components (i) or (ii); and
   d. subjecting said second distillate composition to a third distillation step conducted at a different pressure than the second distillation step in which the component enriched in the second bottoms composition in (c) is removed in a third distillate composition with a third bottoms composition enriched in the same component that was enriched in the second distillate composition;
   wherein said azeotrope or near-azeotrope composition of (b) comprises from about 57.0 mole percent to about 78.0 mole percent E-HFC-1225ye and from about 43.0 mole percent to about 22.0 mole percent hydrogen fluoride.

9. The process of claim 8, further comprising recycling at least some portion of said first bottoms composition to said reaction zone.

10. The process of claim 8, further comprising recycling at least some portion of said second bottoms composition or third bottoms composition to said reaction zone.

11. The process of claim 8, further comprising recycling at least some portion of said second bottoms composition or third bottoms composition to said first distillation step.

* * * * *